(12) United States Patent
Walker et al.

(10) Patent No.: US 9,125,747 B2
(45) Date of Patent: Sep. 8, 2015

(54) IMPLANTS FOR THE TREATMENT OF OSTEOARTHRITIS OF THE KNEE

(71) Applicant: New York University, New York, NY (US)

(72) Inventors: Peter Stanley Walker, New York, NY (US); Joseph A. Bosco, Irvington, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 14/074,056

(22) Filed: Nov. 7, 2013

(65) Prior Publication Data

US 2014/0067079 A1 Mar. 6, 2014

Related U.S. Application Data

(60) Continuation of application No. 13/418,984, filed on Mar. 13, 2012, now Pat. No. 8,603,179, which is a division of application No. 12/577,955, filed on Oct. 13, 2009, now Pat. No. 8,157,868.

(60) Provisional application No. 61/104,336, filed on Oct. 10, 2008, provisional application No. 61/154,980, filed on Feb. 24, 2009.

(51) Int. Cl.
*A61F 2/38* (2006.01)
*A61B 17/16* (2006.01)
(Continued)

(52) U.S. Cl.
CPC ............... *A61F 2/3859* (2013.01); *A61F 2/389* (2013.01); *A61B 17/1675* (2013.01); *A61B 17/1764* (2013.01); *A61B 2017/1602* (2013.01); *A61F 2002/30579* (2013.01); *A61F 2002/30878* (2013.01); *A61F 2002/30884* (2013.01); *A61F 2002/3895* (2013.01);
(Continued)

(58) Field of Classification Search
CPC A61F 2/3859; A61F 2/389; A61F 2002/3895
USPC ....................................................... 623/22.21
See application file for complete search history.

(56) References Cited

U.S. PATENT DOCUMENTS 3,953,899 A 5/1976 Charnley
4,034,418 A 7/1977 Jackson et al.
(Continued)

OTHER PUBLICATIONS

International Search Report for PCT/US2009/060484, mailed Jun. 24, 2010 (5 pages).

*Primary Examiner* — Thomas J Sweet
*Assistant Examiner* — Brian Dukert
(74) *Attorney, Agent, or Firm* — Ann-Louise Kerner; DLA Piper LLP (US)

(57) ABSTRACT

A replacement knee implant has a femoral implant and a tibial implant, each of which are inset in a bone surface. The tibial implant is generally elongated with one end rounded and an opposite end conforming to the shape of the tibia, and is made of a metal alloy or a ceramic. The upper surface is dished while the lower surface is planar and can be parallel or sloped relative to the upper surface. The femoral implant for implementation in a femoral condyle is rounded such that, when implemented, the femoral implant is flush at the anterior and posterior sides and protruding away from the femur between the anterior and posterior ends. The femoral implant can have an elongated keel for extending into the femur, and can be made from a highly cross-linked polyethylene.

11 Claims, 6 Drawing Sheets

(51) Int. Cl.
    *A61B 17/17*     (2006.01)
    *A61F 2/30*      (2006.01)
(52) U.S. Cl.
    CPC .............. *A61F 2310/00023* (2013.01); *A61F 2310/00029* (2013.01); *A61F 2310/00179* (2013.01)

(56) References Cited

U.S. PATENT DOCUMENTS

| | | |
|---|---|---|
| 4,094,017 A | 6/1978 | Matthews et al. |
| 4,340,978 A | 7/1982 | Buechel et al. |
| 4,501,031 A | 2/1985 | McDaniel et al. |
| 4,634,444 A | 1/1987 | Noiles |
| 4,800,639 A | 1/1989 | Frey et al. |
| 5,064,437 A | 11/1991 | Stock et al. |
| 5,171,276 A | 12/1992 | Caspari |
| 5,201,768 A | 4/1993 | Caspari et al. |
| 5,312,411 A | 5/1994 | Steele et al. |
| 5,871,546 A | 2/1999 | Colleran et al. |
| 6,059,831 A | 5/2000 | Braslow et al. |
| 6,206,927 B1 | 3/2001 | Fell et al. |
| 6,558,421 B1 | 5/2003 | Fell et al. |
| 6,652,588 B2 | 11/2003 | Hayes et al. |
| 6,723,102 B2 | 4/2004 | Johnson et al. |
| 6,783,550 B2 | 8/2004 | MacArthur |
| 6,866,684 B2 | 3/2005 | Fell et al. |
| 6,893,463 B2 | 5/2005 | Fell et al. |
| 6,946,001 B2 | 9/2005 | Sanford et al. |
| 6,966,928 B2 | 11/2005 | Fell et al. |
| 7,033,397 B2 | 4/2006 | Webster et al. |
| 7,105,026 B2 | 9/2006 | Johnson et al. |
| 7,105,027 B2 | 9/2006 | Lipman et al. |
| 7,258,701 B2 | 8/2007 | Aram et al. |
| 7,297,161 B2 | 11/2007 | Fell |
| 7,338,524 B2 | 3/2008 | Fell et al. |
| 7,341,602 B2 | 3/2008 | Fell et al. |
| 7,462,198 B2 | 12/2008 | Webster et al. |
| 7,462,199 B2 | 12/2008 | Justin et al. |
| 7,488,324 B1 | 2/2009 | Metzger et al. |
| 7,494,235 B2 | 2/2009 | Fell |
| 7,513,912 B2 | 4/2009 | Hayes, Jr. et al. |
| 7,520,901 B2 | 4/2009 | Engh et al. |
| 7,578,850 B2 | 8/2009 | Kuczynski et al. |
| 7,608,079 B1 | 10/2009 | Blackwell et al. |
| 8,317,869 B2 * | 11/2012 | Cloutier et al. .............. 623/20.3 |
| 2003/0233149 A1 * | 12/2003 | Hodorek .................... 623/20.35 |
| 2004/0204766 A1 | 10/2004 | Siebel |
| 2005/0171612 A1 | 8/2005 | Rolston |
| 2007/0021838 A1 * | 1/2007 | Dugas et al. ................. 623/20.3 |
| 2007/0078517 A1 | 4/2007 | Engh et al. |
| 2007/0299530 A1 | 12/2007 | Rhodes et al. |
| 2008/0058945 A1 | 3/2008 | Hajaj et al. |
| 2008/0119931 A1 | 5/2008 | Fell et al. |
| 2009/0183291 A1 | 7/2009 | Mccall ET AL |

* cited by examiner

IMPLANTS FOR THE TREATMENT OF OSTEOARTHRITIS OF THE KNEE

CROSS-REFERENCE TO RELATED APPLICATIONS

This application is a continuation of U.S. application Ser. No. 13/418,984, filed on Mar. 13, 2012, which is a divisional of U.S. application Ser No. 12/577,955, filed on Oct. 13, 2009 (now U.S. Pat. No. 8,157,868), and claims priority under 35 U.S.C. Section 119(e) to Provisional Application Ser. No. 61/104,336, filed Oct. 10, 2008, and Provisional Application Ser. No. 61/154,980, filed Feb. 24, 2009, all of which are incorporated herein by reference.

FIELD OF THE INVENTION

This disclosure relates to orthopedic knee implants, e.g., for the treatment of osteoarthritis (OA).

BACKGROUND

The earliest implants for the treatment of OA of the knee consisted of fixed metallic hinges at one extreme, and some type of interposition at the other extreme. Interpositions included the use of fascia and other 'soft' biological materials, and also metallic tibial plateaus and metallic shells covering the distal femoral condyles. The 'soft' materials could fail due to inadequate strength and the lack of fixation to the bone. The metallic components fared better. Tibial plateaus, such as those in designs known as MacIntosh and McKeever designs, served to space apart the bearing surfaces, thus potentially correcting the deformity, and provided a smooth bearing surface for the femoral condyles. Lack of fixation of the MacIntosh implant to the tibia sometimes allowed movement or even dislocation, in the McKeever design, the use of keels prevented this problem. The femoral resurfacing devices faced the dual problem of matching the surface geometry of the original intact femur, and of shaping the distal femur to fit the implant. It is believed that obtaining a satisfactory range of motion, as well as stability, would be a problem in many cases due to the geometrical factors noted above. Another issue with such devices, which were not rigidly fixed to the bone, was that there would be 'interface micromotion' leading to resorption of the adjacent bone and replacement with fibrous tissue, leading to residual pain or aching.

This experience with interposition devices pointed to the benefits of rigid fixation of the device to the bone, and to geometrical compatibility within the joint. The question of whether pain resulted from the lack of fixation, or from the opposite side of the joint articulating with a rigid metal surface, was not clear. Clues to that question came from the hip, following the use of Austin-Moore implants for replacement of the femoral head. There was still some residual pain from uncemented femoral components, but far less when the components were cemented. There does not seem to have been a series of knees where a McKeever or a similar device has been fixed to the upper tibia using cement or other means, hence the source of the pain remains in some doubt in the knee. Another question with the use of an interposition device in the knee is the potential wearing away of the cartilage (or even bone) on the opposite side; because the rigidity of the metal caused the contact stresses to be elevated. In the case of a medial metallic tibial plateau, for a shallow bearing surface, the stresses would be significantly elevated. Because in the intact knee, the meniscus would spread the load over a wide area. This fact suggests that the cartilage on the medial femoral condyle could wear out more quickly than in a normal healthy joint.

An implant design of interest was the Gunston, designed in the late 1960's by Frank Gunston from Winnipeg while working as a Fellow at John Charnley's Hip Center in Wrightington, England. A metal half-disc is embedded in the femoral condyle and just projects from it, and is articulated on a plastic runner set into the medial plateau. There was almost complete conformity in the frontal plane, and partial conformity in the sagittal plane.

This configuration had several benefits. The sagittal curve of the femoral condyle could be fairly closely reproduced given sufficient sizes, the slot in the femoral condyle gave a large surface area of strong cancellous bone for cemented fixation, and the tibial surface provided a combination of AP and rotational stability and laxity.

The negatives were that a single sagittal femoral radius could not reproduce the reduced radius in high flexion and the increased radius in extension at the distal end of the femur, cutting a slot in the femoral condyle sometimes endangered the strength of the bone on the outside, and the tibial plateau was of insufficient surface area such that sinkage and loosening occurred, and uncovered bone often impinged on bone on the opposite condyle or abraded against the plastic.

The polycentric knee, as it became known, was used in thousands of cases, especially at the Mayo Clinic, and provided good clinical results in a high percentage of cases.

In the early 1970's, Charnley produced an alternative implant, as shown, for example, in U.S. Pat. No. 3,953,899. Charnley used a thin flat metal plate with a single inner keel for fixation. This approach preserved of most of the strong cortical and sclerotic bone on the upper tibia to maximize the fixation, especially important for a component which did not necessarily cover the entire surface of the medial condyle. Charnley also designed a plastic runner that was embedded into the distal femur. The name 'Load-Angle Inlay' (LAI) described this particular feature of Charnley's implant. The plastic runner was set so that it projected about 2 mm from the surrounding surface but was made to be flush at the anterior and posterior. This arrangement, where the plastic surface was convex and the metal surface was flat, was opposed to the convention of metal-plastic bearings, where the stationary and concave (or flat) component should be plastic and the moving surface metal. The rationale was that the stresses in the convex plastic would be higher potentially leading to delamination wear, and the plastic might wear unevenly which, in the extreme, might cause a discontinuity in the knee motion.

In practice, wear testing would be needed to determine whether the particular configuration used in the Charnley LAI would function well enough for its application, although there appears to be no public records in leading literature for such testing. Minns, Day, and Hardinge (1982) carried out a motion analysis of 29 patients, which indicated satisfactory function, with no mechanical problems being reported.

Another type of knee for medial OA was the unicompartmental or 'uni', introduced in the early 1970's. This design consisted of a metal femoral runner onlaid over the entire arc of the femoral condyle from extension to full flexion. The component design varied from having a curved undersurface to contact the femoral bone after removing any residual cartilage, to a facetted surface requiring flat cuts to be made with an osteotome or saw. The fixation was usually augmented with one or more posts, or blades, or a combination, using cement for immediate and long-term fixation. The tibial component consisted of a hemicircular disc of plastic, sometimes fitting inside a metallic baseplate. The baseplate helps prevent deformation of the plastic in the short and long-term, and the fixation to the bone was more durable. One disadvantage is that more tibial bone needs to be removed to account for the metal, paradoxically having an adverse effect on the fixation due to the fact that the strength of the cancellous bone in the proximal tibia diminishes with depth. As with the femoral component, fixation was by cement, and the undersurface had a combination of posts or blades. On all designs, the upper tibial surface has been close to flat, providing little AP stability, in contrast to the medial surface of the intact knee. This round on flat, or at best cylinder on flat, configuration produces high contact stresses. In long-term follow-ups, for net-shape molded polyethylene, there has typically been a trough formed due to wear and deformation, but no delamination.

An alternate design has been the meniscal bearing uni, where the femoral component had a spherical bearing surface, with the back surface being faceted. The tibial component consisted of a flat metallic plate with a polished upper surface. A plastic meniscus was interposed between the two components and conformed with each. This produced low contact stresses, which minimizes deformation and wear. There was no constraint to AP displacement, other than friction.

The following refers to a study carried out in one of the inventors' laboratory, on the nature of the osteoarthritic lesions at the time of total knee replacement surgery. One of the main purposes of the study was to determine if an early intervention procedure could have been carried out involving only replacement of the medial side of the joint, rather than a total knee. The study of 100 cases was reported to the Orthopaedic Research Society's Annual Meeting in 2007. The predominant lesion of the medial femoral condyle was distal, which is the region which undergoes weight-bearing in walking, by far the most frequent activity of everyday living. The posterior condyle on the other hand was frequently preserved, which makes sense because it is only weight-bearing in the less frequent high flexion activities such as rising from a chair and steep stair climbing. The lateral condyle was usually intact by visual appearance. A later study where the lateral histology was examined, showed that the cartilage structure was normal for that age group of individuals.

On the tibial side, the lesion on the medial plateau varied in location. On the other hand, the lateral side showed normal cartilage on that area covered by the meniscus, but cartilage with some softening and fibrillation on the area not covered by the meniscus. Hence the medial side showed degeneration where a repair was necessary, while the lateral side was frequently normal such that it could sustain normal weight-bearing without need of replacement.

Most of the lesions occurred within the anterior half, the central half, or extended more than one half. A lesser number involved the posterior. When all of the lesions for all 100 cases were superimposed, it was seen that all of the medial tibial plateau could be involved. This indicated that if a single style of tibial component was designed, it would need to cover the whole of the tibial plateau.

SUMMARY

This description relates to knee implants and methods for providing knee implants. The knee implant has two parts—a femoral implant and a tibial implant, each of which has novel features and aspects.

A tibial implant is generally elongated with one end rounded and an opposite end conforming to the shape of the tibia at the anterior side. The upper surface is dished while the lower surface is planar and can be parallel or sloped relative to the upper surface. The lower surface can have a protrusion, such as a keel. The tibial implant is typically about 2-4 mm thick (at its thinnest point) and about 16-24 mm in width. The tibial implant can be made of a metal or other material that allows the implant to be made thin.

The femoral implant for implementation in a femoral condyle is rounded such that, when implemented, the femoral implant is flush at the anterior and posterior sides and protruding away from the femur between the anterior and posterior ends. The femoral implant can have an elongated keel for extending into the femur, and can be made from a highly cross-linked polyethylene.

The description also includes methods for providing the implants, including forming a channel in the tibia that can extent only partway across the top of the tibia, and introducing the tibial implant from the anterior side.

In some embodiments, the tibia is cut at and angle, such as about 5-10 degrees relative to a long axis of the tibia, to allow a reduced bone cut.

Other features and advantages will become apparent from the following description, drawings, and claims.

DESCRIPTION

Figure 1:
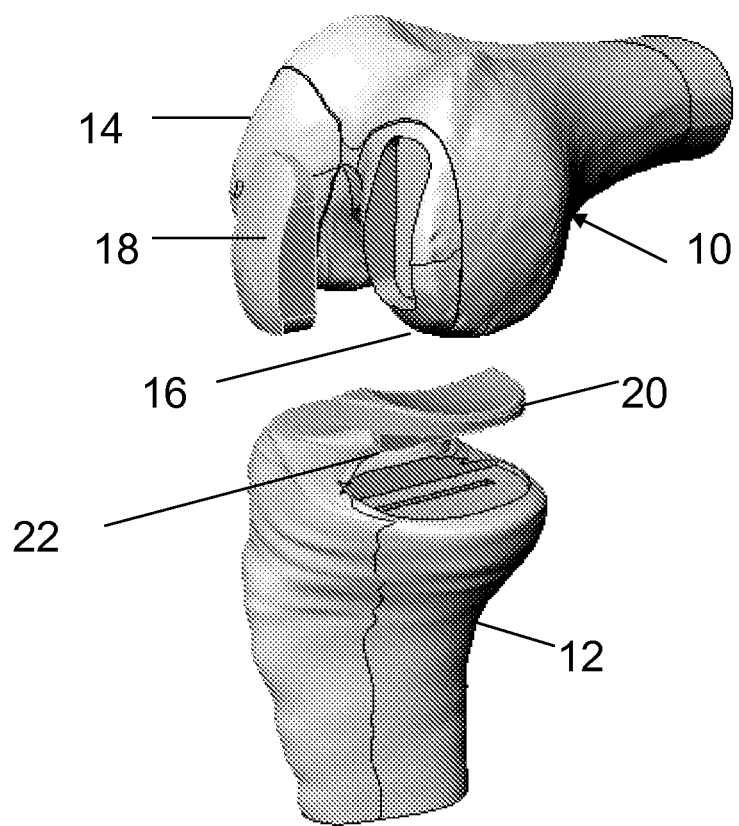
FIG. 1 is a perspective view of a general design concept.

FIG. 1 shows a first general design concept including modifications to a femur 10 and a tibia 12. Femur 10 has a lower end with two condyles 14, 16 for facing the tibia. A portion of condyle 16 has been removed and replaced with an implant 18. The implants have a generally flat face on the inside facing the femur and an outer side that is round to conform to the shape of the rounded condyle. The implant is preferably made of a plastic, such as a highly cross-linked polyethylene.

Tibia 12 has a generally D-shape portion that is removed. A tibial implant 20 has a dished upper surface to provide anterior-posterior (AP) stability and to reduce contact stresses. The tibial insert preferably has at least one keel 22 on the underside for providing support, although two keels could be used. Tibial implant 20 can be formed in one of several different ways, depending on whether there is a small or larger varus (bow-legged) deformity.

If an isolated metallic tibial plateau is used, the bearing surface should be shaped to give maximum conformity with the femoral condyles. In practice this means that there would be conforming surfaces in early flexion, but less conformity in flexion due to the diminishing sagittal radius of the medial femoral condyle. There is not the benefit, as in the intact knee, of a meniscus that can change its shape according to the shape of the femoral condyle itself. A conforming metallic component would require even more rigid fixation to the tibia than a shallow component, because of the high shear and tilting forces that are likely to occur. Another consideration for the shape of the upper surface of a metallic tibial plateau is the required stability on the one hand, and freedom of motion on the other hand. In the intact knee, there are only a few millimeters of AP laxity at all angles of flexion due to the actions of the cruciate ligaments. On the medial side, the stability is further augmented by the dishing of the tibial surface, the menisci, and the medial collateral ligament. Hence from this point of view, the medial dishing of a metallic plateau would be an advantage regarding wear of the medial femoral condyle. Overall however, for durability and absence of pain, replacement bearing surfaces would be needed for both the femur and tibia, and each would need to be rigidly fixed to the bone. For kinematic compatibility, the contours of the artificial surfaces should closely match those of the original femur.

For the treatment of the medial compartment in early OA, where the cruciate ligaments are intact or if adapted in cases where the anterior cruciate is damaged, and where there is no significant varus deformity, there is an additional aspect. A nonlimiting example of a typical knee which would be suitable for this treatment is one where the arthritic lesions are localized on the distal medial femoral condyle, and on the central or anterior regions of the medial tibial plateau. The lateral side of the joint should be able to sustain normal weight-bearing while the patello-femoral joint should show only slight arthritic lesions at most such that there is no significant pain deriving from that compartment. The patients benefiting would be those who still are pursuing an active lifestyle, with a typical age range from 50-65 years. The procedure is envisaged as performed through small incisions and involve much less trauma than a standard total knee replacement, and even less trauma than a standard unicompartmental knee replacement.

Figure 2:
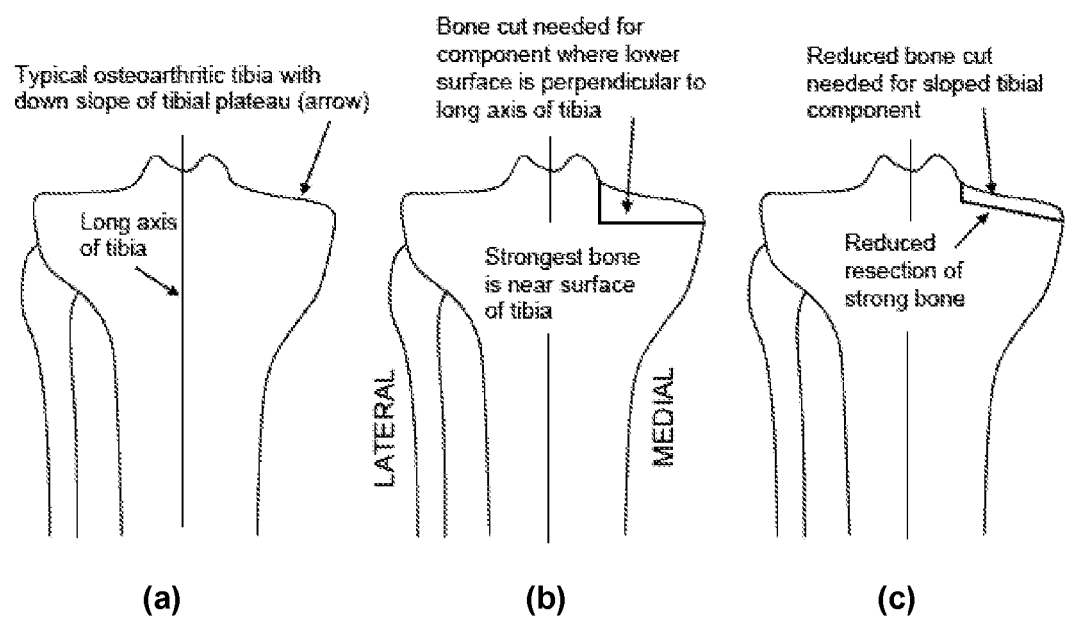
FIGS. 2(*a*)-2(*c*) are side views of different cuts to the tibia.

Referring to FIGS. 2(*a*)-2 (*c*), FIG. 2(*b*) shows a tibia with a bone cut with a lower surface that is perpendicular to a tibial long axis, as is also shown in FIG. 1. One alternative, as shown in FIG. 2(*c*) is to have the lower surface tapered about 5°-10° in the frontal plane to match the bone deformity. This taper can considerably reduce the amount of strong tibial bone that is resected, especially at the inner side of the medial plateau. The surface is tapered to conform better to a tapered surface in the damaged knee.

Figure 3:
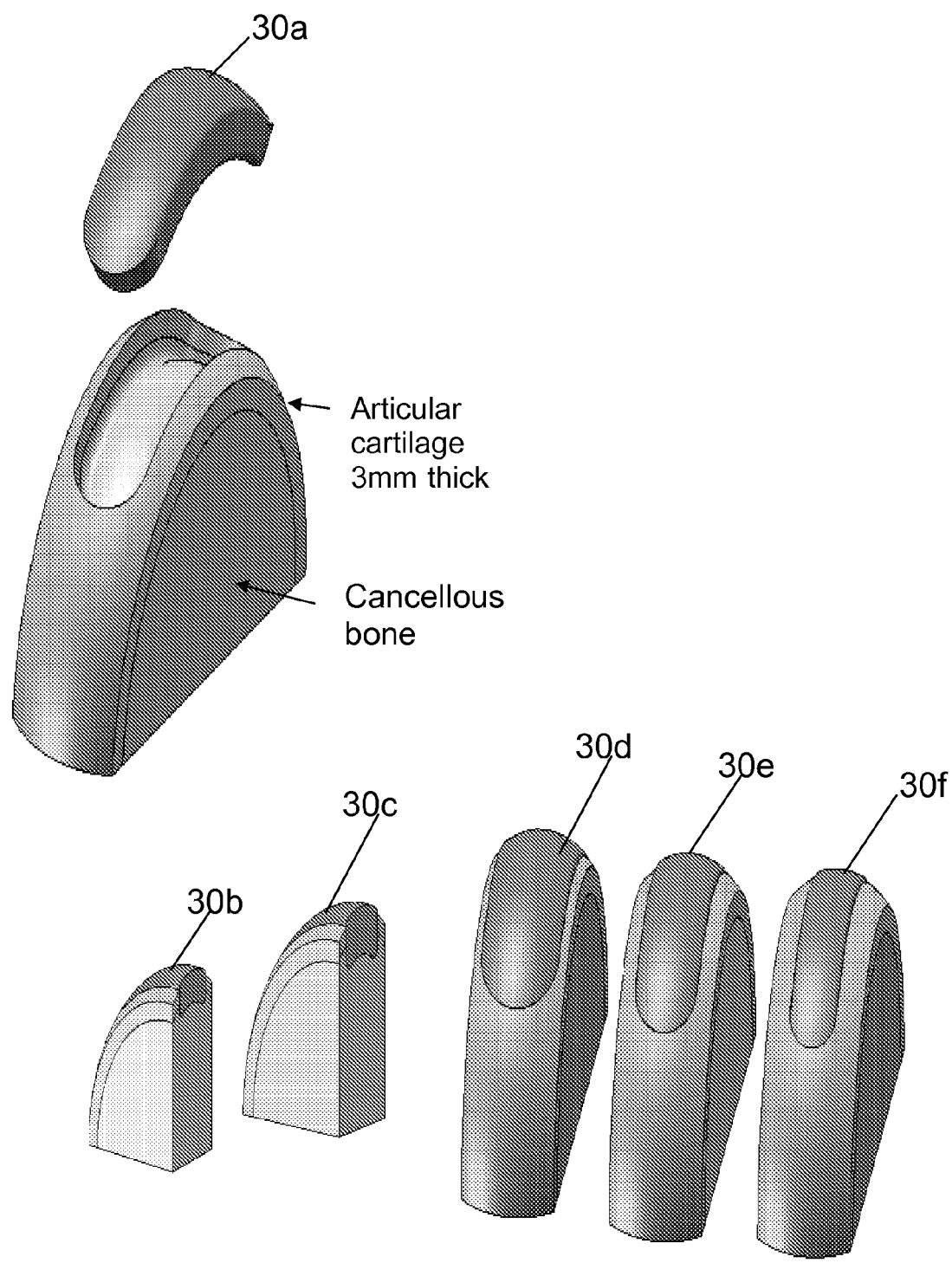
FIG. 3 shows perspective views of embodiments of a femoral implant.
Figure 4:
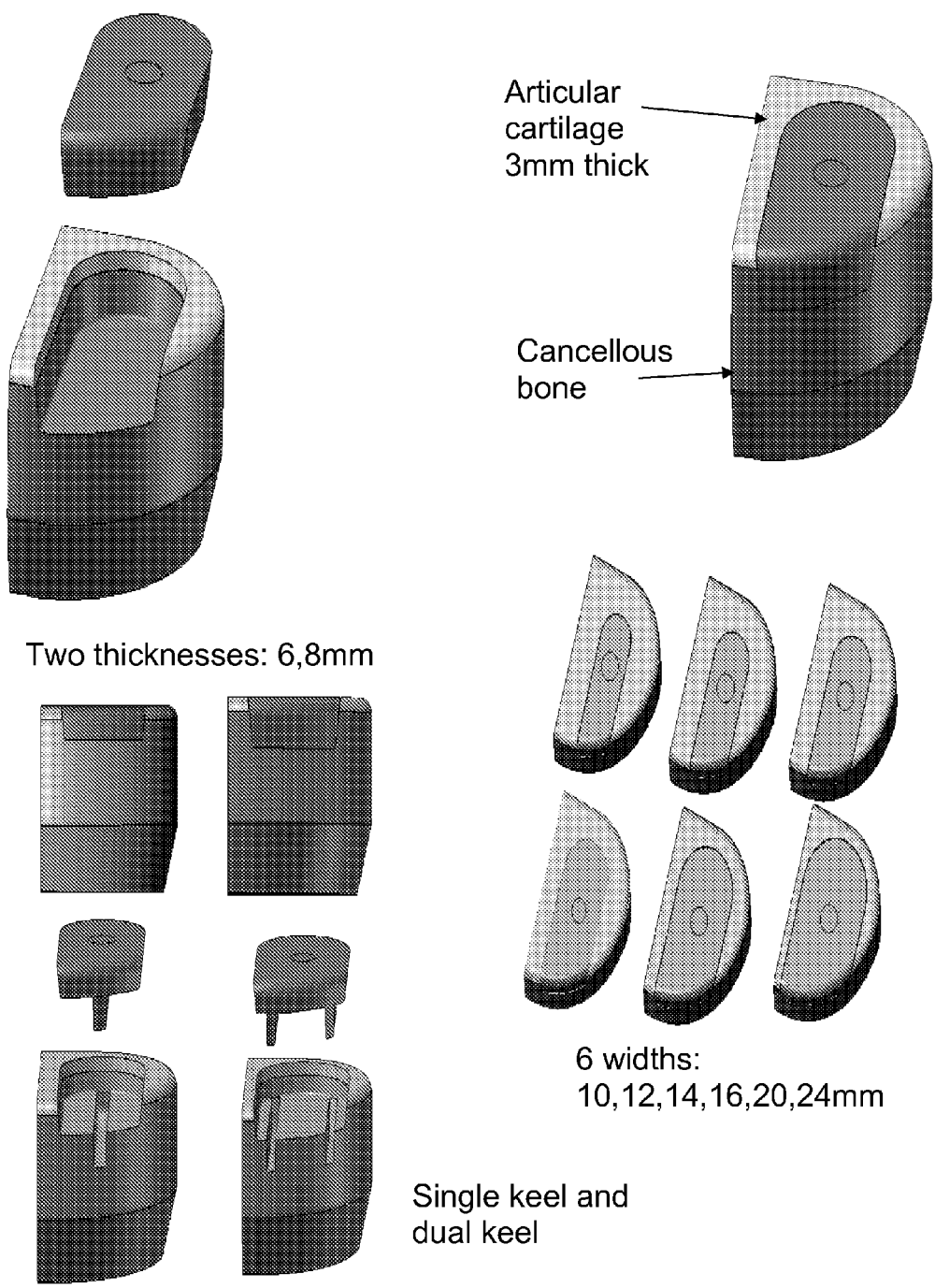
FIG. 4 shows views of embodiments of a tibial implant.
Figure 5:
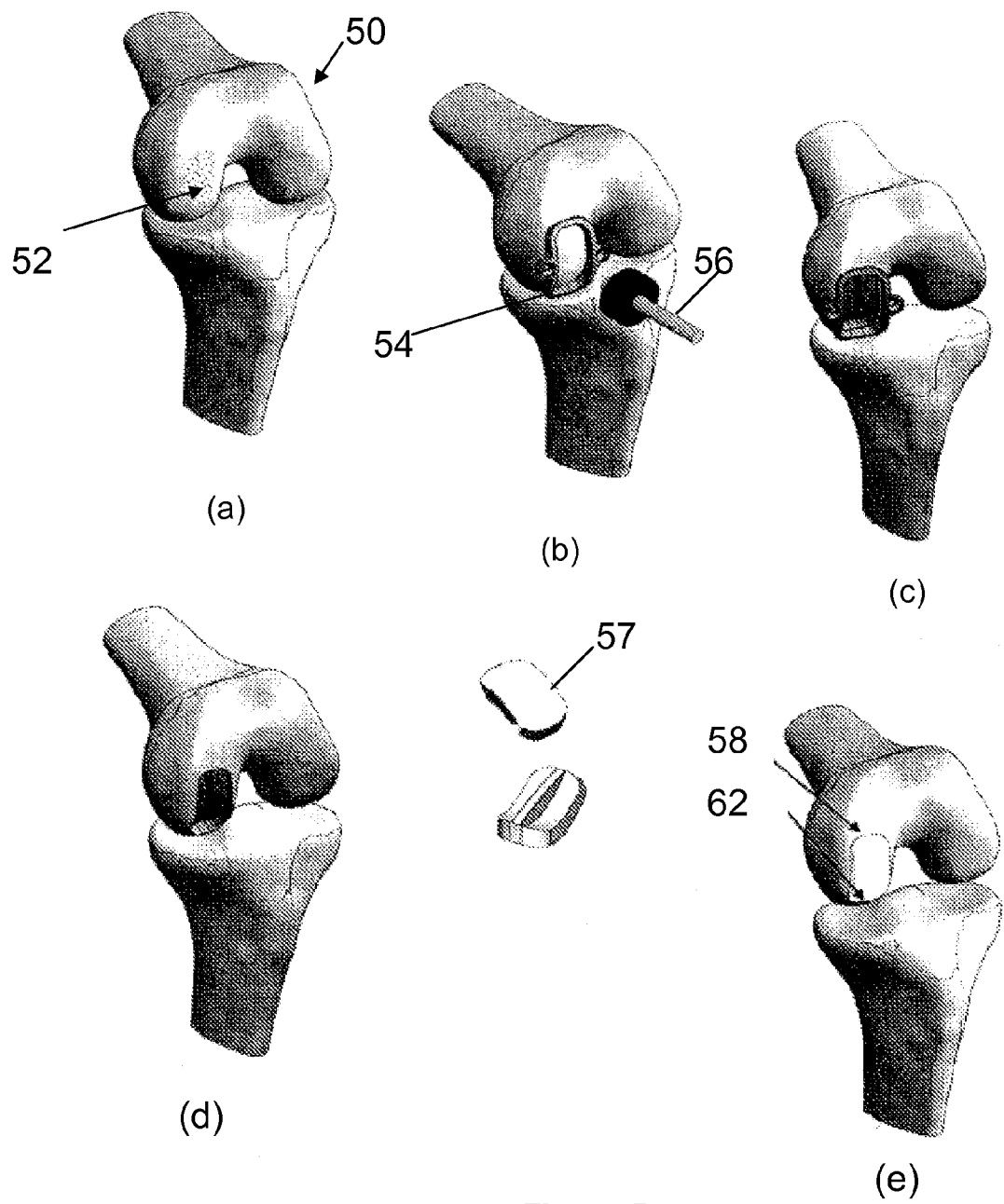
FIGS. 5 and 6 show steps for installing the implants.
Figure 6:
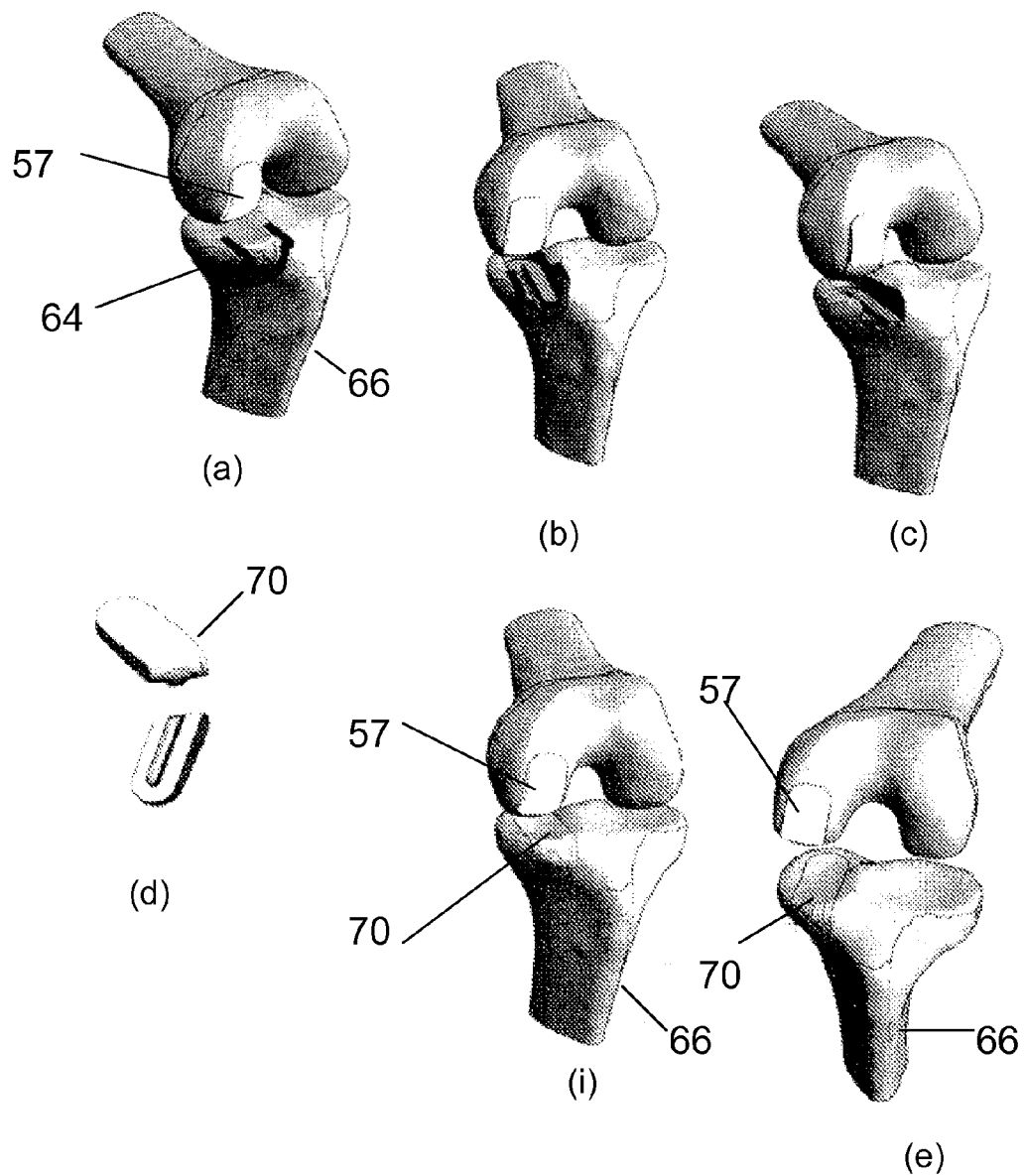

FIGS. 3-6 represent further embodiments that have some of the concepts discussed above, and other features that are different alternatives from those above. FIGS. 3 and 4 are representative drawings of femoral and tibial implants, respectively, and FIGS. 5 and 6 are perspective views showing processes for providing the implants to the knee.

FIG. 3 has figures that represent a portion of the femoral component. Femoral implant 30*a* is designed to have a tight fit in a recess of the femur, which has been machined through cartilage and into bone. Unlike the implant shown in FIG. 1, it has a curve on the inner side that faces the femur. The femoral implant can have various widths, such as 12 mm, 16 mm, or 20 mm width as shown by implants 30*d*, 30*e*, and 30*f*, and is typically 10-14 mm in width; and various thicknesses, such 6 or 8 mm, as shown in implants 30*b* and 30*c*. Different materials can be used for the femoral implant, but preferably it is a plastic, such as ultra high molecular weight polyethylene (UHMWPE).

In one embodiment, the femoral component is made from a wear-resistant polymer such as highly cross-linked polyethylene, with a thickness of at least 8 mm, an optional keel along the base 2-4 mm wide, where the component is inset into the femoral condyle leaving 2-4 mm of bone on each side. The component is sized to carry load from approximately 5 degrees hyperextension to approximately 40-60 degrees flexion. It is flush with the cartilage at the anterior and posterior locations, and projects 0.5-1 mm above the cartilage in the center, the projection tapering down to zero at each end. The projection causes more of the weight-bearing to be in the component and less in surrounding cartilage at each side. The outer radii of the femoral component, in the frontal plane, is about 1-3 mm smaller than that of the tibial component for moderately close conformity and stability. The lower surface of the component can be designed for osseointegration. All edges have a small radius, such as 0.5 mm, to avoid stress concentrations of the bone interfacing with the component.

An advantage of making the femoral component in a polymer is that the tibial component can be made from metal. A metal implant can be made thinner, thus requiring less tibial bone resection. However there are alternate material choices. A molded polyethylene can be used, or a stiff polymer such as polyetheretherketone (PEEK). It is possible to make the femoral component from metal, interfacing with polymer on the tibial side. These are the materials conventionally used today for unicompartmental replacements.

The implant can be fixed to the bone with polymethylmethacrylate cement (PMMA), which is commonly used in knee replacements. Another method is to bond a layer of a porous material such as porous tantalum to the base of the plastic component and rely on subsequent bone ingrowth. The lower surface could also be fused with a trabecular metal for ingrowth fixation. The side and lower surfaces can have grooves to help the bonding.

FIG. 4 illustrates different shapes and sizes of implants for use in a tibia. The tibial implants can have one of several different forms and can have several different shapes. A slot is cut into the tibia from the anterior side, and the implant is introduced anteriorly. The implant is assumed to be bonded to bone (after ingrowth) but not to cartilage. As shown, the device can have different thicknesses, such as 6 mm or 8 mm, can use a single keel or a dual keel for support (1.5-2.5 mm wide and 4-8 mm deep, with lower surface is designed for osseointegration), and can have a width from about 12 to 24 mm, including widths of 10, 12, 14, 16, 20, and 24 mm, or more typically, about 16-24 mm in width. The implant should have a thickness of 2-4 mm at its thinnest point, although higher thicknesses are available, such as 4-10 mm to cope with prevailing bone loss and deformity.

The tibial component can be made from a metal alloy, such as a Co—Cr alloy or a surface hardened titanium alloy, or from a ceramic. The tibial component is inset with 2-4 mm peripheral boundary of cartilage, and with meniscus preserved if applicable, where the bone preparation and component insertion is carried out from the anterior. Although not shown in FIG. 4, the upper surface can be dished with a radius of 50-90 mm, or 60-90 mm, in the sagittal plane to limit the anterior-posterior (AP) displacements and provide AP stability, and a similar dishing in the frontal plane to limit medial-lateral displacements and provide stability, particularly at the interior to match the intercondylar eminence of the anatomic knee. The radius can be about 60 mm anteriorly and 90 mm posteriorly. The top surface can have a high polish for low friction and wear.

The tibial component can be made from different materials. If the femoral component is made from metal, the tibial component can be made from a polymer, such as cross-linked polyethylene or molded polyethylene. It can also have a metal backing to provide greater rigidity and reduce the deformation of the polymer.

Two keels are shown but a single keel is also a viable configuration, especially in cases with strong bone. Using one or two keels can be advantageous because they can avoid the need for a deeper cut into the bone.

The fixation including PMMA or a porous surface, as well as the rounding of corners, as are used for the femoral component. Also, similar to the femoral component, all edges of the tibial component have a small radius to avoid stress concentrations.

FIGS. 5 and 6 show steps in an embodiment of a process. Referring to FIG. 5, an arthritic lesion on a femur 50 is typically in about the location shown at 52. The knee is exposed antero-medially (step a). A femoral fixture 54 is placed over the lesion, and screwed into place. The femoral fixture is available in different sizes and shapes, e.g., 4-6 options (step b). A femoral burr 56 is used to work around fixture 54. A keel slot is then made with a tibial burr. A depth collar of the femoral cutter ensures a uniform depth of pocket (step c). The femoral fixture is removed (step d). The interior periphery of the pocket has a 2-3 mm radius, and the thickness can be about 4-6 mm. A femoral component 57 can have multiple shapes, e.g., 6-8. In this embodiment, it has one keel. The dimensional variables are the sagittal radii, the AP length and the ML width. The component is preferably made from plastic such as UHMWPE. Fixation can be with acrylic cement, or with a fused-in porous material. The femoral component is fixed. The anterior and posterior are flush as shown at 58, while the implant 60 can be protruding in between the ends as shown at 62 (step e).

Referring to FIG. 6, a tibial fixture 64 is pinned to an anterior of a tibia 66 and is aligned with femoral component 57 (step f). The two tags of the fixture 64 determine a depth of cut. A tibial burr is used to make a pocket and a keel slot (step g). The tibial fixture is removed, so the interior periphery of the pocket has a 1-2 mm radius (step h).

The inserted tibial component 70 is compatible with preserving the meniscus, which is released anteriorly to allow access to the component The tibia component can come in different sizes and shapes, e.g., 4-6. The dimensional variables are the sagittal radii, the AP length and the ML width. The component is preferably made from a metal, such as Co—Cr alloy. Fixation can be with acrylic cement, or with a fused-in porous material. The thickness of tibial component is about 2-3 mm. The tibial component is fixed, ensuring that the boundaries are flush or slightly recessed relative to the surrounding cartilage surfaces (step i). As shown here, the tibial implant is generally elongated with one end rounded and an opposite end designed to conform to the shape of the tibia.

In this embodiment, the tibial implant can incorporate aspects of the feature of FIG. 2 where the lower surface is tapered 5-10°.

The compressive stresses on the bone at the base of the recess were calculated using finite element analysis for the normal anatomic knee, and for the different versions of the femoral and tibial components. The criterion was that the normal stresses were the baseline against which to compare the stresses after implantation. If the stresses were higher, that would imply that there was a possibility of compressive bone failure, which would impair the fixation and durability of the implant. On a comparative basis, implants with lower stresses are preferred, all else being equal.

The stresses for the anatomic knee were less than for all of the implants analyzed, including on the femur and tibia. The stresses were approximately inversely proportional to width.

For the femur, the stresses were similar whether plastic or metal was used, for both 6 mm and 8 mm thick components. For the tibia, there was some advantage to using metal for the thinner component. For the tibia, there was a major reduction of stresses using a keel. Using two keels produced a further significant decrease. Rounding the edges of the components, including the keels, avoided stress concentrations at those locations. By insetting components, versus seating on a straight-across resection, was in transmitting shear stresses were transmitted down the peripheral bone contact, hence reducing the stresses on the lower surface of the bone.

What is claimed is:

1. A method of providing a femoral implant to a knee with osteoarthritis, comprising the steps of:
    a. resecting a portion of a femur of a patient, the resected portion comprising an arthritic lesion on a distal medial femoral condyle of the femur;
    b. providing a femoral implant to the resected femur, the implant being at least 8 mm in thickness and having a bearing surface that is convex, the implant being set into the resected femoral condyle such that the implant is flush with the articular surface of the cartilage located at anterior and posterior locations of the knee, the implant projecting above the articular surface of the cartilage in the center of the implant, the projection tapering flush with the articular surface of the cartilage at the medial and lateral edges of the implant.

2. The method of claim 1, wherein the providing step comprises providing the implant to the femur such that when the femoral implant is set into the bone, there is 2 mm to 4 mm of bone on either side of the implant.

3. The method of claim 1, wherein when the femoral implant is set into the knee, the implant projects about 0.5 mm to about 1 mm above the cartilage.

4. The method of claim 1, wherein the femoral implant is fixed to the bone with polymethylmethacrylate cement.

5. The method of claim 1, wherein a lower surface of the femoral implant is bonded to a layer of a porous material to enable bone ingrowth.

6. The method of claim 5, wherein the lower surface of the femoral implant is fused with a trabecular metal.

7. The method of claim 1, wherein the implant has an elongated keel or a peg for extending into the femur.

8. The method of claim 1, wherein the femoral implant comprises a plastic.

9. The method of claim 8, wherein the femoral implant further comprises metal.

10. The method of claim 9, wherein the femoral implant comprises highly cross-linked polyethylene and/or polyetheretherketone (PEEK).

11. The method of claim 1, wherein the femoral implant is about 16 mm to 24 mm in width and about 12 mm to 20 mm in length.

* * * * *